United States Patent [19]

Ohno et al.

[11] Patent Number: 4,496,735

[45] Date of Patent: Jan. 29, 1985

[54] CERTAIN PYRIDYLOXY-OR-THIO-PHENYL PROPENOIC ACID DERIVATIVES

[75] Inventors: Sachio Ohno; Kiyoshi Mizukoshi; Osamu Komatsu; Mitsuaki Nagasaka, all of Aichi; Yoshiki Nakamura, Gifu, all of Japan

[73] Assignee: Maruko Seiyaku Co., Ltd., Nagoya, Japan

[21] Appl. No.: 469,475

[22] Filed: Feb. 24, 1983

[30] Foreign Application Priority Data

Feb. 24, 1982 [JP] Japan .................................. 57-28392

[51] Int. Cl.³ .................. C07D 213/64; C07D 213/65
[52] U.S. Cl. .................................... 546/301; 546/300; 546/302; 514/962
[58] Field of Search ........................ 546/301, 291, 302

[56] References Cited

U.S. PATENT DOCUMENTS 4,216,007 8/1980 Nishiyama et al. ..................... 71/94

FOREIGN PATENT DOCUMENTS 2951786 7/1980 Fed. Rep. of Germany ...... 546/342

OTHER PUBLICATIONS

Ohno et al., Chemical Abstracts, vol. 99, No. 21, Abst. No. 175,598x, Nov. 21, 1983.
Iizuka et al., Journal of Medicinal Chemistry, vol. 24, (10), pp. 1139-1148, (1981).

*Primary Examiner*—Alan L. Rotman
*Attorney, Agent, or Firm*—Sughrue, Mion, Zinn, Macpeak and Seas

[57] ABSTRACT

Novel pyridine compounds and the pharmaceutically acceptable salts thereof having a specific inhibitory activity on thromboxane $A_2$ biosynthesis in mammals useful for prevention and treatment of various disorders caused by thromboxane $A_2$, for example, thrombosis, cardiac infarction, diabetic vascular complications, asthma, etc. are disclosed.

6 Claims, No Drawings

CERTAIN PYRIDYLOXY-OR-THIO-PHENYL PROPENOIC ACID DERIVATIVES

FIELD OF THE INVENTION

This invention relates to novel pyridine compounds and the pharmaceutically acceptable salts thereof having a specific inhibitory activity on thromboxane $A_2$ biosynthesis in mammals useful for prevention and treatment of various disorders caused by thromboxane $A_2$, for example, thrombosis, cardiac infarction, diabetic vascular complications, asthma, etc.

BACKGROUND OF THE INVENTION

Since imidazole was reported as having an inhibitory activity on thromboxane $A_2$ synthetase [Proc. Natl. Acad. Sci., U.S.A., 74 1716 (1977) and Prostaglandins, 13, 611 (1977)], research was made extensively for developing inhibitors on thromboxane $A_2$ synthetase and various imidazole and pyridine compounds have been disclosed in the prior art references, for example, Japanese Patent Publication (Unexamined) Nos. 54-112862, 54-112863, 54-144369, 54-163573, 55-313, 55-28927, 55-85572, 55-100368, 55-47676, 55-89266 and 56-25162; U.S. Pat. Nos. 4,226,878, 4,320,134, 4,317,828 and 4,271,170.

However, these imidazole and pyridine compounds disclosed in the prior art references are generally still not satisfactory in their effects as thromboxane $A_2$ synthetase inhibitors, absorption from digestive tracts and toxicity.

As a result of studies for developing compounds having a strong inhibitory activity on thromboxane $A_2$ synthetase and yet having a low toxicity, the present inventors found that the novel pyridine compounds represented by the formula (I) and their pharmaceutically acceptable salts exhibit an excellent pharmacological activity useful as an inhibitor on thromboxane $A_2$ synthetase.

DETAILED DESCRIPTION OF THE INVENTION

The pyridine compounds of the present invention are represented by the formula

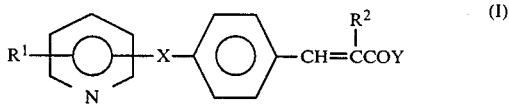

wherein X represents an oxygen atom or a sulfur atom, $R^1$ and $R^2$, which may be the same or different, each represents hydrogen or a straight or branched chain alkyl group having 1 to 3 carbon atoms, Y represents —OH, —OR$^3$ or —NR$^4$R$^5$ wherein R$^3$ represents a straight or branched chain alkyl group having 1 to 4 carbon atoms, R$^4$ and R$^5$, which may be the same or different, each represents hydrogen, a straight or branched chain alkyl group having 1 to 4 carbon atoms or a cycloalkyl group having 3 to 6 carbon atoms, and the pharmaceutically acceptable salts thereof.

Of the pyridine compounds represented by the formula (I) above, a preferred class of compounds is those wherein X represents an oxygen atom or an sulfur atom, $R^1$ and $R^2$, which may be the same or different, each represents hydrogen or a methyl group and Y represents —OH, —OR$^3$ or —NR$^4$R$^5$ wherein R$^3$ represents a methyl group or an ethyl group and R$^4$ and R$^5$, which may be the same or different, each represents hydrogen, a cyclohexyl group or an ethyl group, and the pharmaceutically acceptable salts thereof.

The most preferred compounds of the present invention having the formula (I) include 2-methyl-3-[4-(3-pyridyloxy)phenyl]propenoic acid, 3-[4-(3-pyridyloxy)phenyl]propenoic acid, 2-methyl-3-[4-(3-pyridyloxy)phenyl]propenamide, N-cyclohexyl-2-methyl-3-[4-(3-pyridyloxy)phenyl]propenamide, 2-methyl-3-[4-(4-pyridylthio)phenyl]propenoic acid, methyl 2-methyl-3-[4-(2-pyridylthio)phenyl]propenoate and the like.

The pyridine compounds of the formula (I) can be prepared by the following alternative procedures.

The compounds of the formula (I) wherein Y represents —OH and X, $R^1$, $R^2$ and $R^3$ are as defined above can be prepared by subjecting the benzaldehyde compound of the formula (II)

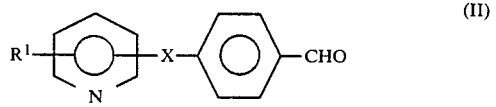

wherein X and $R^1$ are as defined above, to the Perkin reaction using an acid anhydride such as acetic anhydride, propionic anhydride, butyric anhydride, isobutyric anhydride, valeric anhydride and isovaleric anhydride according to the procedure as reported in Organic Reactions, 1, 210 (1942), etc., or by hydrolyzing the compound of the formula (I) wherein Y represents —OR$^3$ and X, $R^1$, $R^2$ and $R^3$ are as defined above, in an inert solvent such as water, an alcohol such as methanol, ethanol, isopropanol and the like or a mixture thereof in the presence of an acid such as sulfuric acid, hydrochloric acid and the like, or a base such as sodium hydroxide, potassium hydroxide and the like.

The above Perkin reaction can be conducted using 1 mol to a molar excess of an acid anhydride per mol of the benzaldehyde compound (II) at a temperature of 140° to 190° C. for a period of 1 to 10 hours.

The hydrolysis of the ester (I: Y=—OR$^3$) to the corresponding carboxylic acid compound (I: Y=—OH) can be carried out at a temperature of 70° to 100° C. for a period of 1 to 10 hours.

The compounds of the formula (I) wherein Y represents —OR$^3$ and X, $R^1$, $R^2$ and $R^3$ are as defined above can be prepared by subjecting the benzaldehyde of the formula (II) to the Wittig reaction or to a reaction similar to the Wittig reaction as reported in Organic Reactions, 14, 270 (1965). More specifically, the above compounds (I) can be prepared by reacting the benzaldehyde compound of the formula (II) with an ester represented by the formula (III)

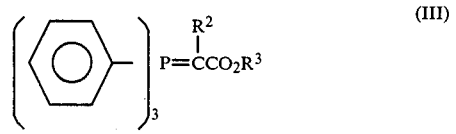

wherein $R^2$ and $R^3$ are as defined above, or with an anion obtained from the ester represented by the formula (IV)

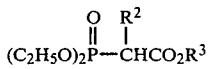 (IV)

wherein $R^2$ and $R^3$ are as defined above, in an inert organic solvent such as diethyl ether, tetrahydrofuran, benzene and the like. The anion obtained from the above ester (IV) has the following formula

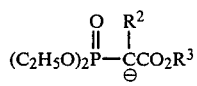

The reaction between the benzaldehyde (II) and the ester (III) or an anion of the ester (IV) can be conducted using about 1 mol to a molar excess of the ester (III) or the anion of the ester (IV) per mol of the benzladehyde (II) at a temperature of 0° to 50° C. for a period of 1 to 5 hours.

Alternatively, the compound of the formula (I) wherein Y represents $-OR^3$ can be prepared by esterifying the corresponding carboxy compound (Y = —OH) with an alcohol having 1 to 4 carbon atoms of the formula $R^3OH$ wherein $R^3$ is as defined above in the presence of an acid catalyst such as hydrogen chloride, sulfuric acid, etc. by a conventional procedure for esterification of a carboxylic acid. The above esterification can be generally achieved using a large molar excess of the alcohol ($R^3OH$) per mol of the compound (I) at a temperature of 60° to 100° C. for a period of 0.5 to 3 hours.

The compounds of the formula (I) wherein Y represents $-NR^4R^5$ and X, $R^1$, $R^2$, $R^4$ and $R^5$ are as defined above, can be prepared by reacting an acid chloride represented by the formula (V)

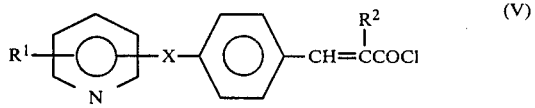 (V)

wherein X, $R^1$ and $R^2$ are as defined above, with an amine represented by the formula $R^4R^5NH$ wherein $R^4$ and $R^5$ are as defined above, in the absence or presence of an inert organic solvent such as benzene, diethyl ether, chloroform, dichloromethane and the like.

The reaction between the acid chloride (V) and the amine ($R^4R^5NH$) can be achieved using about 2 mols to a molar excess of the amine per mol of the acid chloride (V) at a temperature of from −10° C. to 30° C. for a period of 0.5 to 3 hours. In this reaction, the amine can be used in an excess amount so as to serve as a reactant and also as a reaction solvent.

The acid chloride of the formula (V) used in the above reaction can be prepared by reacting a compound of the formula (I) wherein Y represents —OH and X, $R^1$ and $R^2$ are as defined above, with a chlorinating agent such as thionyl chloride in the absence or presence of an inert organic solvent such as benzene, chloroform and the like. This chlorination reaction can be achieved at a temperature of 30° to 80° C. for a period of 0.5 to 4 hours.

The pharmaceutically acceptable salts of the compounds of the formula (I) include non-toxic acid addition salts and metal salts of the carboxyl group. Preferred examples of the salts are hydrochloride, hydrobromide, sulfate, phosphate, sodium salt, potassium salt, calcium salt, aluminum salt and the like.

The benzaldehyde compounds of the formula (II) above used as starting materials for preparing the compounds of the formula (I) are novel compounds and can be easily prepared by reacting an aldehyde represented by the formula (VI)

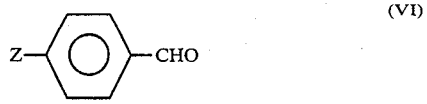 (VI)

wherein Z represents a halogen atom such as a chlorine atom or a bromine atom, with a pyridine compound represented by the formula (VII)

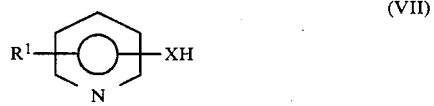 (VII)

wherein X and $R^1$ are as defined above, or by reacting an aldehyde represented by the formula (VIII)

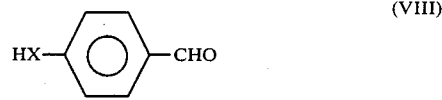 (VIII)

wherein X is as defined above, with a pyridine compound represented by the formula (IX)

 (IX)

wherein $R^1$ and Z are as defined above, in an inert solvent such as dimethylformamide, dimethyl sulfoxide, hexamethylphosphoramide and the like in the presence of a base such as potassium carbonate, sodium carbonate and the like.

The compounds of the present invention having the formula (I) and the pharmaceutically acceptable salts thereof thus obtained have a strong inhibitory activity on thromboxane $A_2$ synthetase. A typical in vivo test method for evaluating compounds which may be useful as a so-called anti-thrombotic agent has been reported in literature and this method comprises determining the prevention of sudden death of rabbits caused by arachidonic acid, as reported in, for example, Agents and Actions, 7, 481 (1977); Pharmacology, 14, 522 (1976); Science, 183, 1085 (1974), etc.

More specifically, sodium arachidonate is administered intravenously to rabbits at a dose of about 1.4 mg/kg to cause a sudden death within a few minutes due to platelet aggregation and lung embolus. The compounds of the present invention of the formula (I) exhibit strong prevention of the sudden death in rabbits caused by arachidonic acid and, therefore, are very useful as pharmaceutical agents for prevention and treatment of the above-described disorders which are considered to be induced by thromboxane $A_2$.

The compounds of the present invention can be administered to mammals including human orally or parenterally, e.g., intravenously or intrarectally, alone or in admixture with other pharmaceutical carriers, excipients, binders, lubricants and the like, in dosage forms such as tablets, granules, powders, capsules, injectable preparations and the like. Examples of suitable carriers, excipients, binders, lubricants, etc. for formulating into the above dosage forms include starch, dextrin, sucrose, lactose, silicic acid, carboxymethyl cellulose, cellulose, gelatin, polyvinyl pyrrolidone, glycerin, agar, calcium carbonate, sodium bicarbonate, paraffin, cetyl alcohol, stearic acid ester, kaolin, bentonite, talc, calcium stearate, magnesium stearate, polyethylene glycol, water, ethanol, isopropyl alcohol, propylene glycol and the like.

The dosage level of the compounds of the formula (I) and their pharmaceutically acceptable salts is usually in the range of from about 0.1 to 60 mg/kg of body weight per day by oral administration and from 0.01 to 0.4 mg/kg of body weight per day by intravenous administration, either in a single dose or multiple doses, but the dosage level can, of course, be reduced or increased appropriately depneding upon the severity of conditions to be treated, the age of patients and other various factors.

The present invention is further illustrated in greater detail by the following Examples and Reference Examples, but is not limited to these examples.

EXAMPLE 1

A mixture of 5 g of 4-(2-methyl-5-pyridyloxy)benzaldehyde, 5 g of sodium propionate and 35 ml of propionic anhydride was stirred for 3 hours at a temperature of 150° to 155° C. and then concentrated under reduced pressure. Water was added to the mixture which was then heated to crystallize the product. The resulting crystals were separated by filtration, washed with water and recrystallized from a mixture of acetic acid and water to obtain 3.3 g (52% yield) of 2-methyl-3-[4-(2-methyl-5-pyridyloxy)phenyl]propenoic acid as colorless needles having a melting point of 211°–213° C. Recrystallization from a mixture of methanol and isopropyl alcohol yielded colorless prisms having a melting point of 211°–214° C.

NMR (CD$_3$OD)δ: 2.13 (3H, d, J=1.0 Hz), 2.81 (3H, s), 7.27 (2H, A2B2 type d, J=8.5 Hz), 7.56 (2H, A2B2 type d, J=8.5 Hz), 7.70 (1H, br s), 7.93 (1H, d, J=9.0 Hz), 8.21 (1H, dd, J=9.0 & 2.3 Hz), 8.53 (1H, d, J=2.3 Hz).

IR (KBr) cm$^{-1}$: 1689 (CO).

EXAMPLE 2

A mixture of 6 g of 4-(2-pyridylthio)benzaldehyde, 6 g of sodium propionate and 30 ml of propionic anhydride was stirred for 5 hours at a temperature of 150° to 155° C. and then concentrated under reduced pressure. Water was added to the mixture which was then heated. The mixture was allowed to stand to precipitate crystals and the resulting crystals were separated by filtration, washed with water and dried to obtain 2-methyl-3-[4-(2-pyridylthio)phenyl]propenoic acid. The product was dissolved in 30 ml of methanol, and a small amount of methanolic hydrogen chloride was added to the solution, followed by refluxing for 1 hour. The solvent was distilled off and the resulting crystals were recrystallized from a mixture of methanol and ethyl acetate to obtain 2.6 g (30% yield) of methyl 2-methyl-3-[4-(2-pyridylthio)phenyl]propenoate hydrochloride as colorless needles having a melting point of 130°–133° C.

NMR (CD$_3$OD)δ: 2.14 (3H, d, J=1.1 Hz), 3.83 (3H, s), 7.37–8.00 (7H, m), 8.33 (1H, td, J=8.0 & 1.3 Hz), 8.70 (1H, dd, J=8.0 & 1.3 Hz)

EXAMPLE 3

3 g of sodium hydride (50%) was added to 50 ml of tetrahydrofuran and 10 g of triethyl 2-phosphonopropionate was added dropwise to the mixture. A solution of 7.0 g of 4-(2-methyl-5-pyridyloxy)benzaldehyde in 20 ml of tetrahydrofuran was added dropwise to the mixture, followed by stirring for 3 hours. Diethyl ether and water were added to the reaction mixture and the organic layer was separated, washed with water and extracted with 10% hydrochloric acid. The aqueous layer was washed with diethyl ether, rendered alkaline with sodium carbonate and extracted with diethyl ether. The ether layer was washed with water and dried over magnesium sulfate. The solvent was distilled off and the resulting oily substance was purified by silica gel chromatography (eluted with dichloromethane-hexane, 1:1 to 2:1 by volume) to obtain 6.0 g (61% yield) of ethyl 2-ethyl-3-[4-(2-ethyl-5-pyridyloxy)phenyl]propenoate as a colorless oil having a boiling point of 170° C./2 mmHg (bath temperature).

NMR (CDCl$_3$)δ: 1.33 (3H, t, J=7.0 Hz), 2.11 (3H, d, J=1.6 Hz), 2.55 (3H, s), 4.28 (2H, q, J=7.0 Hz), 6.84–7.58 (6H, m), 7.65 (1H, br s), 8.31 (1H, d like).

EXAMPLE 4

A mixture of 5 g of 4-(4-pyridylthio)benzaldehyde hydrochloride, 4 g of sodium propionate and 50 ml of propionic anhydride was stirred for 5 hours at a temperature of 150° to 155° C. and concentrated under reduced pressure. Water was added to the mixture which was then heated to precipitate crystals. The resulting crystals were separated by filtration, washed with water and converted into the corresponding hydrochloride by treatment with methanolic hydrogen chloride. The resulting hydrochloride was recrystallized from a mixture of methanol and diethyl ether to obtain 3.4 g (56% yield) of 2-methyl-3-[4-(4-pyridylthio)phenyl]propenoic acid hydrochloride as colorless needles having a melting point of 213°–218° C.

NMR (CD$_3$OD)δ: 2.13 (3H, d, J=1.2 Hz), 7.47–7.87 (6H, m), 8.37–8.63 (2H, m).

EXAMPLE 5

A mixture of 7 g of 4-(3-pyridyloxy)benzaldehyde, 4 g of sodium propionate and 8 ml of propionic anhydride was heated at a temperature of 135° to 140° C. for 2 hours. After allowing the mixture to cool, the mixture was rendered alkaline with an aqueous solution of sodium hydroxide, washed with dichloromethane and rendered acidic with acetic acid. The precipitated crystals were separated by filtration, washed with water and recrystallized from methanol to obtain 5 g (56% yield) of 2-methyl-3-[4-(3-pyridyloxy)phenyl]propenoic acid as colorless prisms having a melting point of 191°–194° C.

NMR (DNSO-d$_6$)δ: 2.06 (3H, br s), 7.15 (2H, A2B2 type d, J=9.0 Hz), 7.40–7.75 (5H, m), 8.26–8.60 (2H, m).

The corresponding hydrochloride salt was prepared in the same manner as described in Example 4 and recrystallized from a mixture of isopropyl alcohol and methanol. Colorless needles having a melting point of 198°–204° C.

EXAMPLE 6

5 g of thionyl chloride was added dropwise to a mixture of 6 g of 2-methyl-3-[4-(3-pyridyloxy)phenyl]propenoic acid, 80 ml of pyridine and 50 ml of chloroform under ice-cooling with stirring, followed by stirring for one hour to obtain a solution of 2-methyl-3-[4-(3-pyridyloxy)phenyl]propenoic acid chloride. 8 g of cyclohexylamine was added to the solution, and the mixture was stirred for one hour and poured into water. The mixture was rendered basic with sodium carbonate, and the organic layer was separated by filtration, washed with water and dried over magnesium sulfate. The solvent was distilled off and the resulting oily substance was purified by silica gel chromatography (eluted with chloroform-diethyl ether, 1:2 by volume). The resulting crystals were converted into the hydrochloride in the same manner as described in Example 4 and recrystallized from a mixture of ethanol and diethyl ether to obtain 4.5 g (51% yield) of N-cyclohexyl-2-methyl-3-[4-(3-pyridyloxy)phenyl]propenamide hydrochloride having a melting point of 162°–166° C.

NMR (CD$_3$OD)$\delta$: 0.90–2.23 (13H, m, 2.06 (3H, d, J=1.4 Hz)), 3.43–4.03 (1H, m), 7.17 (1H, br s), 7.26 (2H, A2B2 type d, J=8.8 Hz), 7.53 (2H, A2B2 type d, J=8.8 Hz), 7.87–8.23 (2H, m), 8.48–8.83 (2H, m).

Following the procedures described in Examples 1 to 6, the following compounds (Examples 7 to 10) were also prepared.

EXAMPLE 7

Ethyl 2-methyl-3-[4-(3-pyridyloxy)phenyl]propenoate. Colorless oil. Boiling point: 173° C./2–3 mmHg.

NMR (CDCl$_3$)$\delta$: 1.36 (3H, t, J=7.0 Hz), 2.10 (3H, d, J=1.5 Hz), 4.27 (2H, q, J=7.0 Hz), 7.06 (2H A2B2 type d, J=8.5 Hz), 7.26–7.80 (5H, m), 8.32–8.50 (2H, m).

EXAMPLE 8

2-Methyl-3-[4-(3-pyridyloxy)phenyl]propenamide hydrochloride. Recrystallized from a mixture of methanol and diethyl ether. Colorless needles. Melting point: 184°–189° C.

NMR (CD$_3$OD)$\delta$: 2.12 (3H, d, J=1.5 Hz), 7.33 (2H, A2B2 type d, J=8.5 Hz), 7.40(1H, br s), 7.60 (2H, A2B2 type d, J=8.5 Hz), 7.97–8.44 (2H, m), 8.57–8.85 (2H, m).

EXAMPLE 9

3-[4-(3-Pyridyloxy)phenyl]propenoic acid. Recrystallized from a mixture of chloroform and isopropyl alcohol. Colorless needles. Melting point: 205°–208° C.

NMR (DMSO-d$_6$)$\delta$: 6.53 (1H, d, J=15.0 Hz), 7.13 (2H, A2B2 type d, J=8.5 Hz), 7.35–7.80 (3H, m), 7.59 (2H, A2B2 type d, J=8.5 Hz), 8.30–8.65 (2H, m).

The corresponding hydrochloride was recrystallized from a mixture of ethanol and diethyl ether. Colorless prisms. Melting point: 157°–161° C.

EXAMPLE 10

N,N-Diethyl-2-methyl-3-[4-(3-pyridyloxy)phenyl]propenamide. Colorless oil. Boiling point: 210°–211° C./2 mmHg (bath temperature).

NMR (CDCl$_3$)$\delta$: 1.24 (6H, t, J=7.0 Hz), 2.14 (3H, d, J=1.5 Hz), 3.47 (4H, q, J=7.0 Hz), 6.52 (1H, br s like), 7.05 (2H, A2B2 type d, J=9.0 Hz), 7.23–7.55 (4H, m), 8.30–8.55 (2H, m).

REFERENCE EXAMPLE 1

A mixture of 25 g of 2-methyl-5-pyridinol, 32 g of 4-chlorobenzaldehyde, 75 g of potassium carbonate and 200 ml of dimethylformamide was heated under refluxing for 6 hours with stirring. After cooling, the mixture was filtered and the filtrate was concentrated. The resulting oily substance was dissolved in diethyl ether, and the solution was washed successively with an aqueous solution of sodium hydroxide and water, and dried over magnesium sulfate. The solvent was then distilled off and the resulting oily substance was dissolved in isopropyl alcohol. To the solution was added concentrated hydrochloric acid, and the resulting hydrochloride was filtered and recrystallized from a mixture of methanol and ethyl acetate to obtain colorless needles. The crystals were added to an aqueous solution of sodium carbonate and the mixture was extracted with dichloromethane. The organic layer was washed with water and dried over magnesium sulfate. The solvent was distilled off to obtain an oily substance which crystallized upon standing. The crystals were recrystallized from hexane to obtain 17 g (35% yield) of 4-(2-methyl-5-pyridyloxy)benzaldehyde as colorless prisms having a melting point of 45°–46° C. and a boiling point of 133° C./2 mmHg (bath temperature).

NMR (CDCl$_3$)$\delta$: 2.55 (3H, s), 6.93–7.50 (4H, m, 7.07 (2H, A2B2 type d, J=8.9 Hz)), 7.83 (2H, d, J=8.9 Hz), 8.33 (1H, m), 9.91 (1H, s).

REFERENCE EXAMPLE 2

A mixture of 18.4 g of 2-pyridinethiol, 23.2 g of 4-chlorobenzaldehyde, 40 g of potassium carbonate and 100 ml of hexamethylphosphoramide was heated at a temperature of 140° C. for 4 hours. After cooling, the mixture was filtered and the filtrate was concentrated. The resulting oily substance was dissolved in diethyl ether and the solution was washed successively with an aqueous solution of sodium hydroxide and water, and dried over magnesium sulfate. The solvent was distilled off and the resulting oily substance was distilled under reduced pressure to obtain 15 g (42% yield) of 4-(2-pyridylthio)benzaldehyde as a colorless oil having a boiling point of 136° C./2 mmHg.

NMR (CDCl$_3$)$\delta$: 6.93–8.03 (7H, m, 7.64 (2H, A2B2 type d, J=9.7 Hz), 7.82 (2H, A2B2 type d, J=9.7 Hz)), 8.37–8.63 (1H, m), 9.99 (1H, s).

REFERENCE EXAMPLE 3

A mixture of 25 g of 3-bromopyridine, 20 g of 4-hydroxybenzaldehyde, 60 g of potassium carbonate and 150 ml of hexamethylphosphoramide was heated at a temperature of 130° to 135° C. for 11 hours. After cooling, the mixture was poured into water and extracted with diethyl ether. The ether extract was washed with water and extracted with 10% hydrochloric acid. The aqueous layer was washed with diethyl ether, rendered alkaline with sodium hydroxide and extracted with diethyl ether. The ether extract was washed with water and dried over sodium sulfate. The solvent was distilled off and the resulting oily substance was purified by silica gel chromatography (eluted with diethyl ether) to obtain 13.9 g (45% yield) of 4-(3-pyridyloxy)benzaldehyde as a colorless oil having a boiling point of 135°–140° C./2–3 mmHg.

NMR (CDCl$_3$)$\delta$: 7.14 (2H, A2B2 type d, J=8.5 Hz), 7.35–7.55 (2H, m), 7.90 (2H, A2B2 type d, J=8.5 Hz), 8.35–8.65 (2H, m), 9.95 (1H, s).

IR (neat) cm$^{-1}$: 1685 (CO).

REFERENCE EXAMPLE 4

In the same manner as described in Reference Examples 1 to 3, 4-(4-pyridylthio)benzaldehyde hydrochloride was prepared. Recrystallized from a mixture of methanol and diethyl ether. Colorless needles. Melting point: 216°–222° C.

NMR (CD$_3$OD): 7.47–7.83 (6H, m, 7.69 (4H, s)), 8.40–8.67 (2H, m).

The pharmacological activities and acute toxicity of typical examples of the compounds (I) of the present invention are described hereinafter in detail in comparison with some prior art compounds. The compounds used in the experimentations are as follows:

Compound A: Nonylimidazole [Biochem. Biophys. Res. Commun., 80, 236 (1978)]

Compound B: 4-(2-Imidazol-1-ylethoxy)benzoic acid hydrochloride (Japanese Patent Publication (Unexamined) No. 55-85572)

Compound C: 2-Methyl-3-[4-(3-pyridylmethyl)-phenyl]propenoic acid hydrochloride (Japanese Patent Publication (Unexamined) No. 55-89266)

Compound D: 2-Methyl-3-[4-(3-pyridyloxy)phenyl]-propenoic acid hydrochloride (Example 5 of Present Invention)

Compound E: N-Cyclohexyl-2-methyl-3-[4-(3-pyridyloxy)phenyl]propenamide hydrochloride (Example 6 of Present Invention)

Compound F: 2-Methyl-3-[4-(4-pyridylthio)phenyl]-propenoic acid hydrochloride (Example 4 of Present Invention)

Compound G: 2-Methyl-3-[4-(3-pyridyloxy)phenyl]-propenamide hydrochloride (Example 8 of Present Invention)

Effect on Arachidonic Acid-Induced Sudden Death in Rabbit

According to the method of Silver et al [Science, 183, 1085 (1974)], 20 mg/kg of the test compound was administered intraperitoneally into male rabbits (8 or 10 rabbits per group), each weighing 2.2 to 2.8 kg, and 2 hours after the administration 1.4 mg/kg of sodium arachidonate was administered to the rabbit from an ear vein. The mortality of the rabbits was then calculated 30 minutes after the administration of sodium arachidonate. The results obtained are shown in Table 1 below.

TABLE 1

| Test Compound | Ratio of Mortality/Total Number | % Protection |
| --- | --- | --- |
| A | 5/10 | 50 |
| D | 0/10 | 100 |
| E | 2/8 | 75 |

As is apparent from the results shown in Table 1, the compounds (I) of the present invention (Compounds D and E) exhibit a strong protection against the arachidonic acid-induced sudden death in rabbits.

Inhibition of Thromboxane A$_2$ Synthesis

Rabbit platelet-rich plasma (PRP, 6×10$^8$ platelets/ml) and the test compound was pre-incubated at 37° C. for 5 minutes and, after adding collagen to the mixture at a concentration of 13 ug/ml, the resulting mixture was incubated at 37° C. for 5 minutes. Then, the reaction was terminated by rendering the mixture neutral with hydrochloric acid and the amount of thromboxane B$_2$ produced was quantitatively determined by the radioimmunoassay. The 50% inhibitory concentration (IC$_{50}$) was shown in Table 2 below.

Inhibition of Platelet Aggregation

Rabbit platelet-rich plasma was pre-incubated at 37° C. for 1 minute and, after adding the test compound, arachidonic acid or collagen was added thereto at a concentration of 100 ug/ml or 10 ug/ml, respectively. The aggregation of platelets was recorded using an aggregometer and shown in Table 2 in terms of IC$_{50}$ value.

TABLE 2

| Test Compound | IC$_{50}$ on Thromboxane A$_2$ Synthesis (μM) | Inhibition of Platelet Aggregation | |
| --- | --- | --- | --- |
| | | Arachidonic Acid | Collagen |
| B | 5.7 | >1000 | 400 |
| C | 0.22 | >1000 | 420 |
| D | 1.0 | — | 36 |
| E | 5.9 | 31 | 47 |
| F | 0.31 | — | 22 |
| G | 0.56 | 335 | 56 |

As is apparent from the results shown in Table 2, the compounds (I) of the present invention exhibit a strong inhibitory activity on thromboxane A$_2$ synthesis. Also, the compounds (I) of the present invention exhibit a strong inhibitory activity on platelet aggregation induced by arachidonic acid and collagen.

On the other hand, the comparative Compounds B and C have only a very weak inhibitory activity on platelet aggregation.

Acute Toxicity

The test compound was administered intraperitoneally to ddY male mice weighing 22 to 24 g and LD$_{50}$ was determined by the Behrens-Kärber method [Arch. exp. Path. Pharmak., 177, 379 (1935)] from the mortality one week after administration. The results obtained are shown in Table 3 below.

TABLE 3

| Test Compound | LD$_{50}$ (mice; i.p.) mg/kg |
| --- | --- |
| A | 59 |
| C | 220 |
| D | 350 |
| E | 210 |
| G | 310 |

PREPARATION EXAMPLES

Capsules

Capsules each containing the following formulation was prepared in a conventional manner.

| | |
| --- | --- |
| Compound C | 100 mg |
| Carboxymethyl Cellulose Calcium | 20 mg |
| Calcium Stearate | 5 mg |
| Crystalline Cellulose | 50 mg |
| Talc | 10 mg |
| Total | 185 mg |

Tablets

Tablets each containing the following formulation was prepared in a conventional manner.

| | | |
|---|---|---|
| Compound A | 100 mg | |
| Lactose | 100 mg | |
| Starch | 30 mg | |
| Crystalline Cellulose | 40 mg | |
| Magnesium Stearate | 1 mg | |
| Total | 271 mg | |

Granules

Granules having the following formulation were prepared in a conventional manner and filled in usual twin-shell capsules.

| | | |
|---|---|---|
| Compound D | 100 mg | |
| Lactose | 400 mg | |
| Starch | 50 mg | |
| Crystalline Cellulose | 14 mg | |
| Talc | 5 mg | |
| Total | 555 mg/capsule | |

While the invention has been described in detail with reference to specific embodiments thereof, it will be apparent to one skilled in the art that various changes and modifications can be made therein without departing from the spirit and scope of the invention.

What is claimed is:

1. A pyridine compound represented by the formula

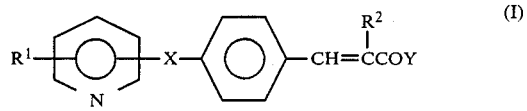

wherein X represents an oxygen atom or a sulfur atom, $R^1$ and $R^2$, which may be the same or different, each represents hydrogen or a straight or branched chain alkyl group having 1 to 3 carbon atoms, Y represents —OH or —$OR^3$ wherein $R^3$ represents a straight or branched chain alkyl group having 1 to 4 carbon atoms, and the pharmaceutically acceptable salts thereof.

2. A pyridine compound according to claim 1, wherein X represents an oxygen atom or a sulfur atom, $R^1$ and $R^2$, which may be the same or different, each represents hydrogen or a methyl group and Y represents —OH or —$OR^3$ wherein $R^3$ represents a methyl group or an ethyl group, and the pharmaceutically acceptable salts thereof.

3. 2-Methyl-3-[4-(3-pyridyloxy)phenyl]propenoic acid and the pharmaceutically acceptable salt thereof according to claim 1.

4. 3-[4-(3-Pyridyloxy)phenyl]propenoic acid and the pharmaceutically acceptable salt thereof according to claim 1.

5. 2-Methyl-3-[4-(4-pyridylthio)phenyl]propenoic acid and the pharmaceutically acceptable salt thereof according to claim 1.

6. Methyl 2-methyl-3-[4-(2-pyridylthio)phenyl]propenoate and the pharmaceutically acceptable salt thereof according to claim 1.

* * * * *